US00PP36717P2

(12) United States Plant Patent
Evison

(10) Patent No.: US PP36,717 P2
(45) Date of Patent: Jun. 3, 2025

(54) ***CLEMATIS* PLANT NAMED 'EviGsy152'**

(50) Latin Name: ***Clematis patens* X *viticella***
Varietal Denomination: EviGsy152

(71) Applicant: Raymond J. Evison Ltd., Vale (GB)

(72) Inventor: Raymond J. Evison, Vale (GB)

(73) Assignee: RAYMOND J. EVISON LTD., Vale (GB)

( * ) Notice: Subject to any disclaimer, the term of this patent is extended or adjusted under 35 U.S.C. 154(b) by 0 days.

(21) Appl. No.: 18/534,867

(22) Filed: Dec. 11, 2023

(51) Int. Cl.
*A01H 5/02* (2018.01)
*A01H 6/72* (2018.01)

(52) U.S. Cl.
USPC ..... Plt./228
CPC ..... *A01H 6/72* (2018.05); *A01H 5/02* (2013.01)

(58) Field of Classification Search
USPC ..... Plt./228
CPC ..... A01H 5/02; A01H 5/00; A01H 6/72
See application file for complete search history.

(56) References Cited

PUBLICATIONS

CPVO Application Consultation Version 4.20.15 retrieved on Nov. 5, 2024 at https://online.plantvarieties.eu/publicConsultationDetails?registerId=20240477&denomination=evigsy152, 2 pp. (Year: 2024).*

* cited by examiner

*Primary Examiner* — June Hwu
(74) *Attorney, Agent, or Firm* — Penny J. Aguirre

(57) ABSTRACT

A new cultivar of *Clematis* plant named 'EviGsy152' that is characterized by its large sized flowers (up to 14 cm in diameter), its flowers that are deep blue-purple in color with contrasting red-purple anthers, its star-shaped flowers, its repeat flowering from May through July and again in September, its floriferous blooming habit with an abundance of flowers, and its high suitability for use in gardens and containers.

3 Drawing Sheets

Botanical classification: *Clematis patens* X *viticella*.
Variety denomination: 'EviGsy152'.

BACKGROUND OF THE INVENTION

The present invention relates to a new and distinct cultivar of *Clematis* of hybrid origin (Patens Group) and will be referred to hereafter by its cultivar name 'EviGsy152'. 'EviGsy152' is grown as an herbaceous climbing plant for use in the landscape or as a flowering potted plant for the terrace.

'EviGsy152' derived from an ongoing breeding program by the Inventor in his nursery in Guernsey, The Channel Islands. The goal of the breeding program is to select new cultivars of *Clematis* with a compact plant habits with an abundance of flowers that are large in size with unique flower colors. 'EviGsy152' was selected as a single unique plant in May of 2019 and arose from a controlled cross made in June of 2014 between unnamed seedlings of *Clematis patens* X *viticella* from the Inventor's breeding program.

Asexual propagation of the new cultivar was first accomplished by stem cuttings under the direction of the Inventor in Guernsey, The Channel Islands in May of 2019. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'EviGsy152' as a unique cultivar of *Clematis*.

1. 'EviGsy152' exhibits large sized flowers (up to 14 cm in diameter).
2. 'EviGsy152' exhibits flowers that are deep blue-purple in color with contrasting red- purple anthers.
3. 'EviGsy152' exhibits star-shaped flowers.
4. 'EviGsy152' exhibits repeat flowering from May through July and again in September.
5. 'EviGsy152' exhibits a floriferous blooming habit with an abundance of flowers.
6. 'EviGsy152' exhibits high suitability for use in gardens and containers.

The female parent of 'EviGsy152' differs from 'EviGsy152' in having flowers with lighter colored sepals. The male parent of 'EviGsy152' differs from 'EviGsy152' in flowers with slightly darker blue-purple tepals and yellow anthers. 'EviGsy152' can be most closely compared to the *Clematis* cultivars 'The President' (not patented) and 'Evipo019' (U.S. Plant Pat. No. 16,069). 'The President' is similar to 'EviGsy152' in sepal and anther color. 'The President' differs from 'EviGsy152' in having a less compact plant habit, a less floriferous blooming habit, and foliage that becomes flushed with a red-brown coloration. 'Evipo019' is similar to 'EviGsy152' in having a compact plant habit. 'Evipo019' differs from 'EviGsy152' in having flowers with tepals that are lighter in color and a slightly taller plant height.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Raymond Evison *Clematis* Donahue's Greenhouse, Horticulture Week, GTN Extra, Commercial Horticulture Association, Gardenforum, Plantago, Weibo, Bluestone Perennials, BPnieuws, Wildon Brothers Gardens, Gardens of the world, Le Rose di Firenze, Hayloft Plants, ForalDaily, and Griffin Greenhouse Supplies.

BRIEF DESCRIPTION OF THE DRAWINGS

The accompanying color photographs illustrate the overall appearance and distinct characteristics of the new *Clematis*. The photographs were taken of 2.5-year-old plants of 'EviGsy152' as grown in a 17-cm container in Guernsey, The Channel Islands.

The photograph in FIG. 1 provides a view of a plant of 'EviGsy152' in bloom.

Figure 1:
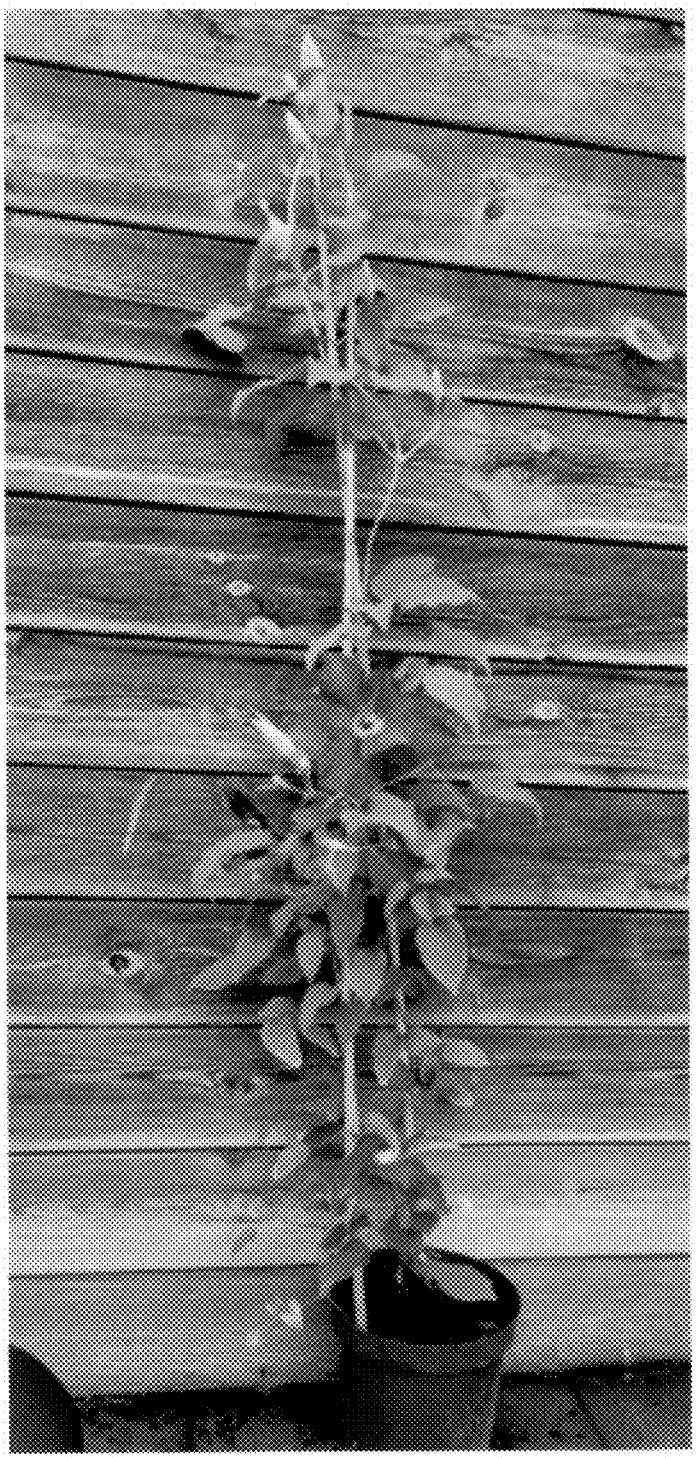
Figure 2:
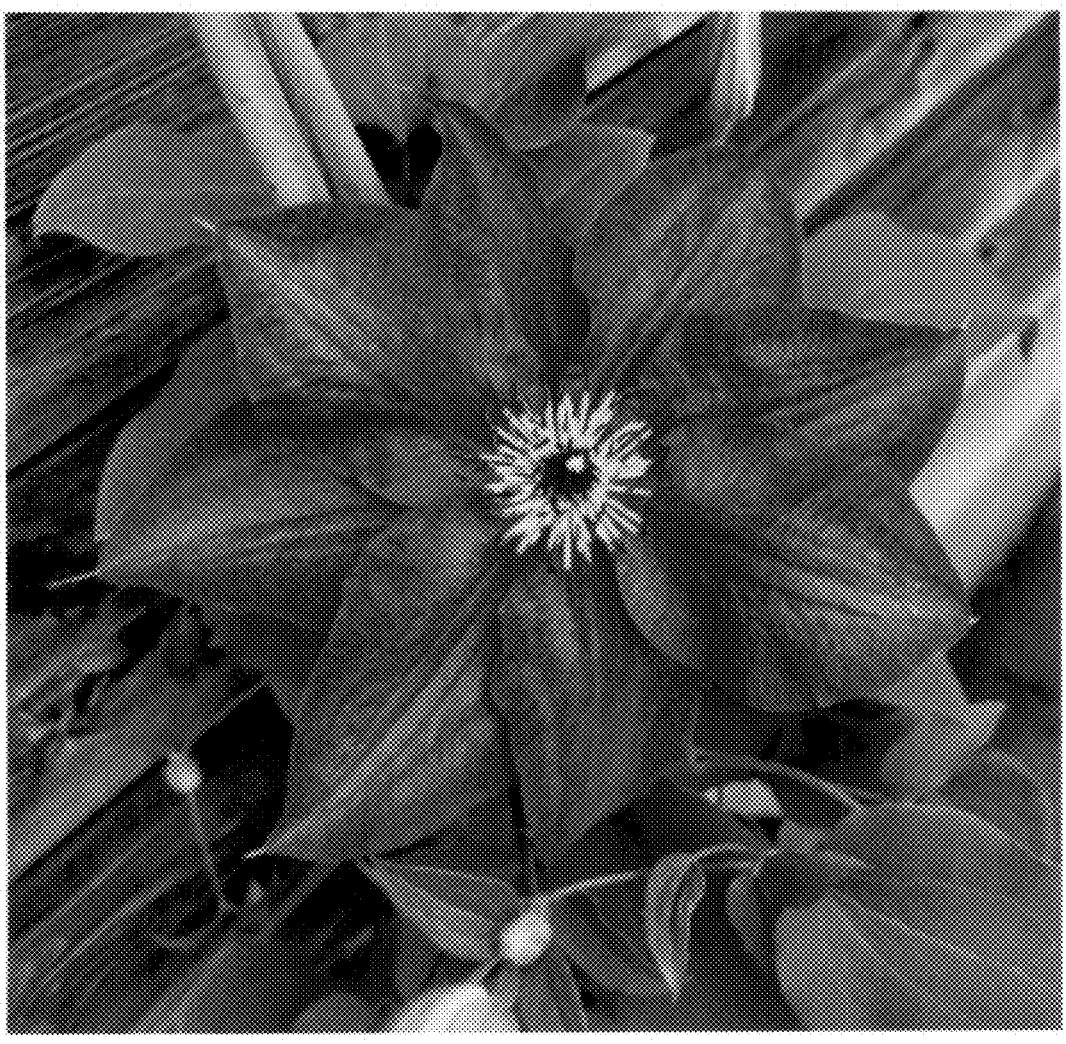

The photograph in FIG. 2 provides a close-up view of a flower of 'EviGsy152'.

Figure 3:
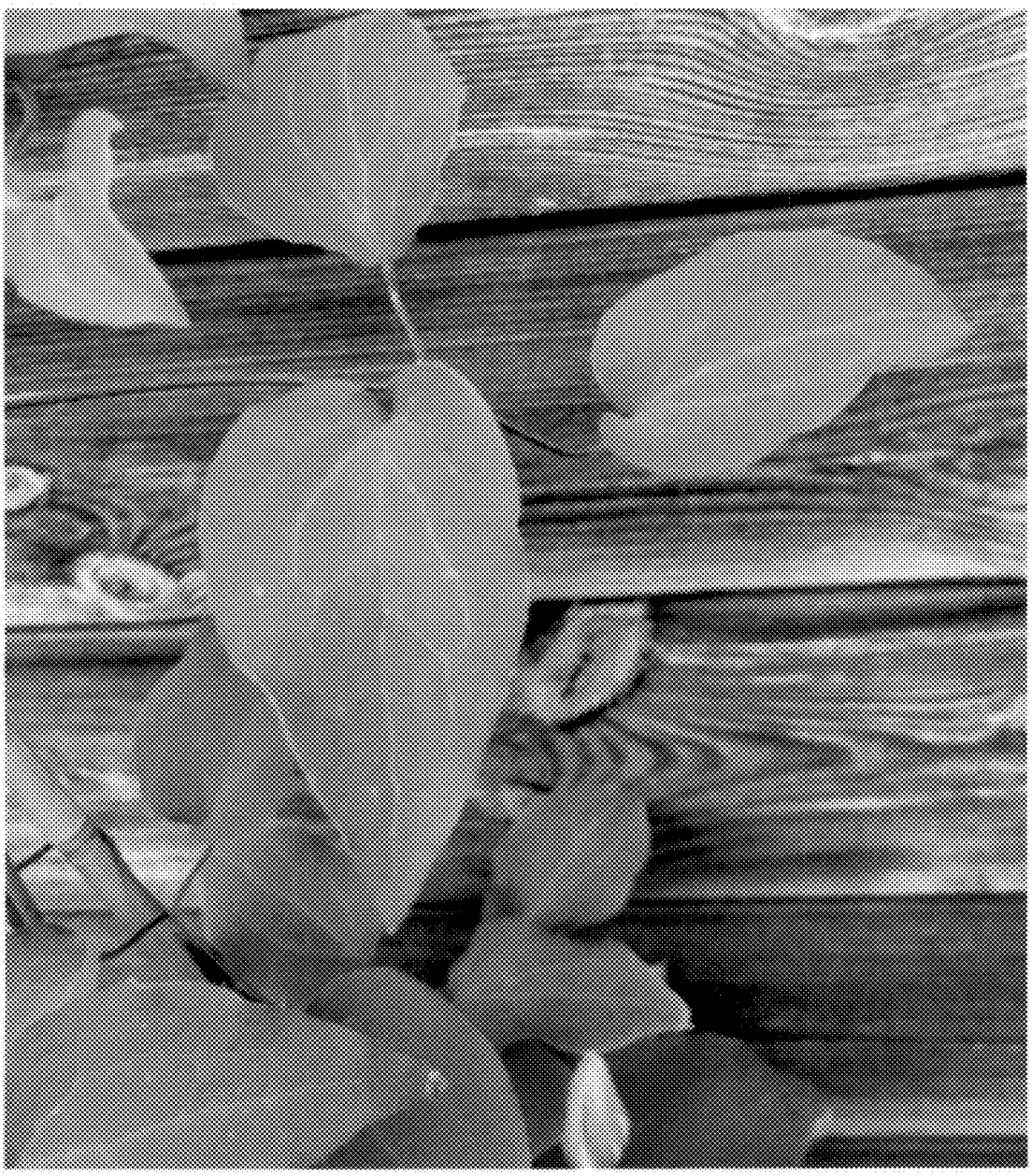

The photograph in FIG. 3 provides a close-up view of a leaf of 'EviGsy152'.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 2.5-year-old plants of 'EviGsy152' as grown in 17-cm containers in Guernsey, The Channel Islands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period*.—Blooms from May through July and reblooms in September in Guernsey, The Channel Islands.
- *Plant type*.—Herbaceous woody vine, large flowering *Clematis* that blooms on both old and new wood.
- *Plant habit*.—Climber, stems emerge from base, compact.
- *Height and spread*.—Average of 1.2 m in height and 36 cm in spread as a 2.5 year-old plant grown in a container, seasons growth in the landscape attains 90 to 120 cm in height and 50 to 60 cm in spread.
- *Cold hardiness*.—At least to U.S.D.A. Zone 5.
- *Diseases*.—No susceptibility or resistance to pests and diseases has been observed.
- *Root description*.—Fleshy.
- *Propagation*.—Softwood cuttings from vegetative shoots.
- *Time required for root initiation*.—Root initiation takes 3 months, 3 to 4 weeks for roots to appear, another 4 to 6 weeks to produce a fully rooted cutting ready for potting, root development from plug to P7 is 3 to 6 months, 30 weeks for mature plant in a P12 container.
- *Growth rate*.—Moderate.
- *Plant vigor*.—Medium.

Stem description:

- *Shape*.—Round.
- *Stem color*.—Young; 144C, mature; 144C with 187A, older stems; 200D.
- *Stem size*.—Length from base to flowering portion of the stem; 49 cm in length, 3 mm in diameter.
- *Stem surface*.—Sparsely pubescent.
- *Stem strength*.—Strong.
- *Internode length*.—Average of 7 cm.
- *Branching*.—Basal branching, average of 3 main branches.

Foliage description:

- *Leaf arrangement*.—Opposite, ternate.
- *Leaf division*.—Compound.
- *Leaf attachment*.—Petiolate.
- *Leaf quantity*.—10 per stems, 3 leaflets per leaf.
- *Leaf size*.—Average of 13 cm in length and 14 cm in width.
- *Leaflet shape*.—Ovate.
- *Leaflet base*.—Rounded.
- *Leaflet apex*.—Acute.
- *Leaflet fragrance*.—None.
- *Leaflet venation*.—Palmate, color; young upper and lower surface 144C, mature upper 137D, mature lower 144A, mid-rib 137C.
- *Leaflet margins*.—Entire.
- *Leaflet attachment*.—Petiolule.
- *Leaflet surface*.—Upper surface glabrous, lower surface matte.
- *Leaflet size*.—Average of 7 cm in length and 6 cm in width.
- *Leaflet color*.—Young upper surface; 144B, young lower surface 144B, mature upper surface 137C, mature lower surface 137D.
- *Petioles*.—Up to 7 cm in length, 2 mm in width, 145A, flushed with 183B, sparsely pubescent surface.
- *Petiolules*.—Up to 4 cm in length, 1 to 2 mm in diameter, 145A, flushed with 183B, sparsely pubescent surface.

Inflorescence description:

- *Inflorescence type*.—Solitary.
- *Inflorescence arrangement*.—Terminal and axillary on new growth.
- *Pedicel*.—2.5 cm in length, 3 mm in diameter, 145A in color, glabrous surface, moderate strength.
- *Bud description*.—Ovoid in shape, 3.2 cm in length, 1.3 cm in width, 145C to 145D in color, pubescent surface.
- *Flower fragrance*.—No
- *Lastingness of flowers*.—Individual flowers last about 10 days, self-cleaning.
- *Flower quantity*.—2 open flowers, 14 buds.
- *Flower type*.—Single, rotate, spreading, star-shaped.
- *Flower aspect*.—Outward, rotate.
- *Flower size*.—Up to 14 cm in width, 3.5 cm in depth.
- *Tepal number*.—8.
- *Tepal shape*.—Broadly elliptic.
- *Tepal apex*.—Acuminate.
- *Tepal base*.—Acute.
- *Tepal margins*.—Entire, very light undulations.

*Tepal surface*.—Both surfaces glabrous, satiny, matte.

*Tepal color*.—Young and mature upper surface; 93B, around mid-rib 93C to 93D, 97C to 97D in the middle extending to apex, and slightly suffused with N81B at the base, young and mature lower surface; 93B, around mid-rib 93C to 93D, midrib 145A, apex 145C to 145D.

*Tepal size*.—Average of 6 cm in length and 4.8 cm in width.

*Tepal arrangement*.—Overlapping.

*Tepal curvature in longitudinal section*.—Moderately reflexed to flat.

*Receptacle*.—7 mm in depth, 9 mm in width, pubescent surface, round in shape, 144B in color.

Reproductive organs:

*Gynoecium*.—Pistils; around 70, style; 2 cm in length, 1 mm in diameter, color; 157D, stigma; slightly superior relative to the length of the filaments and height of the anthers, very small, ovary; 144A.

*Androecium*.—Stamens; 120 to 150, filaments; 1.2 cm in length, glabrous surface, NN155A, 93B to 93C in color, anthers; 5 mm in length, elongated in shape, 187A to 187B in color, glabrous, pollen was not observed.

*Seed*.—Seed head; an average of 2.5 cm in length, 3.6 cm in width, shiny hairs, style; plumose at base, color; 144A to 144B and 165A to 165B, seed development was not observed.

It is claimed:

1. A new and distinct cultivar of *Clematis* plant named 'EviGsy152' as herein illustrated and described.

* * * * *